United States Patent [19]

Haas et al.

[11] 4,147,515

[45] Apr. 3, 1979

[54] ELECTRO-CHEMICAL SENSORS FOR GAS DETECTION IN ELECTRON TUBES

[75] Inventors: George A. Haas, Alexandria, Va.; Richard F. Greene, Bethesda; Arnold Shih, Gaithersburg, both of Md.

[73] Assignee: The United States of America as represented by the Secretary of the Navy, Washington, D.C.

[21] Appl. No.: 863,363

[22] Filed: Dec. 22, 1977

[51] Int. Cl.² ............................................ G01N 27/04
[52] U.S. Cl. ................................ 23/232 E; 73/27 R; 338/34; 422/98
[58] Field of Search ..................... 23/232 E, 254 E; 338/34; 73/23, 27 R; 324/71 R

[56] References Cited

U.S. PATENT DOCUMENTS

| | | |
|---|---|---|
| 3,778,229 | 12/1973 | Webster et al. .................. 23/254 E |
| 3,924,219 | 12/1975 | Braun .............................. 23/254 E X |
| 3,955,929 | 5/1976 | Kawakami et al. ............... 23/254 E |
| 4,015,230 | 3/1977 | Nitta et al. ...................... 23/254 E X |
| 4,045,178 | 8/1977 | Okinaka et al. .................. 23/254 E |

Primary Examiner—R. E. Serwin
Attorney, Agent, or Firm—R. S. Sciascia; Philip Schneider; William C. Daubenspeck

[57] ABSTRACT

An electro-chemical gas sensor for use in electron tubes comprising a crystalline body of BaO formed on a non-interacting (chemically and electrically) substrate and at least two electrodes. The change in conductivity of the barium oxide upon exposure to tube gases may be used to determine the type and quantity of gases contaminating the electron emitter and estimate changes in the emitter's work function or electron emission capability due to gas contamination.

10 Claims, 7 Drawing Figures

ELECTRO-CHEMICAL SENSORS FOR GAS DETECTION IN ELECTRON TUBES

BACKGROUND OF THE INVENTION

This invention relates in general to gas detection and especially to gas detection in electron tubes. More particulatly, this inv ention relates to electro-chemical sensors which can measure the presence of gases in electron tubes and determine changes in the work function or electron emission capability in electron tubes due to gas contamination.

The contamination of the electron emitters by residual gases or the outgassing of absorbed or occluded constitutents is a serious problem in vacuum tubes. In particular, tube gases may build up while a tube is in storage and the resultant poisoning of the electron emitter by these gases is a major cause of tube failure during turn-on. Very low concentrations of some of these tube gases will change the work function of the electron emitter causing the tube to fail, while much larger concentrations of other gases will not significantly degrade a tube's performance. Therefore, it is desirable to monitor the build-up of various tube gases in vacuum tubes and to obtain information as to the type and concentration of these gases.

In the past, ordinary chemical gas-sensing techniques that utilize changes in visual appearance (e.g., the color change of getter flash or litmus-type indicators) have been employed. These are usually ineffective in sensing the low concentrations of gases that can change an emitter's work function and do not distinguish between types of gases. Gas analysers or ion gauges have been used to monitor tube gases, but these devices, in addition to being large, complex, and expensive, may not have the required sensitivity or distinguish between harmful and harmless gases. Actual work function measurements may be taken using the tube's cathode or an auxiliary cathode; however, this requires heating the cathode to thermionic temperatures or may involve turning the entire tube on. These latter techniques also alter the true gas content of the tube by ion-pumping and by generating additional gases.

SUMMARY OF THE INVENTION

The present invention provides a simple and inexpensive sensor for detecting the gases which may contaminate electron tubes. The sensitivity of the sensor may be chosen based on the requirements of a particular application and, to a limited extent, the type of gas contaminating the tube may be determined. The sensor can not only measure the amount of contaminating gas but can predict the change in the work function or degradation of the electron emitter due to poisoning by the tube gases. This is accomplished in a non-destructive manner without requiring actual work function measurements or energizing the tube.

The present invention is based on the discovery that when an activated barium oxide (BaO) emitter is poisoned by gases typically found in vacuum tubes, the change in the work function of the emitter is due to a change in the position of the conduction-band edge $E_c$ with respect to the Fermi level of the surface. The change in the position of the conduction-band edge is related to the number of gas molecules that have contaminated the surface. Since the crystal conductivity of a material is also related to the position of the conduction-band edge, changes in crystal conductivity of an activated BaO sensor which is exposed to the tube gas may be used to indicate the quantity of gas contaminating the electron emitter and predict changes in the emitter's work function.

In general, an electro-chemical sensor according to this invention comprises a body of activated BaO formed on a non-interacting substrate (both chemically and electrically non-interacting). Electrodes are coupled to the BaO so that an inter-electrode volume is defined between the electrodes. Gas molecules that enter this inter-electrode volume will change the crystal conductivity. This conductivity may be determined from a plot of the sensor current versus the potential applied between the electrodes. In addition, the sensor will typically have a means for heating the BaO body to permit control of the temperature at which the conductivity is measured.

Other features and advantages of this invention will be readily appreciated as the same becomes better understood by reference to the following detailed description when considered in conjunction with the accompanying drawings wherein:

DESCRIPTION OF THE PREFERRED EMBODIMENT

Figure 1:
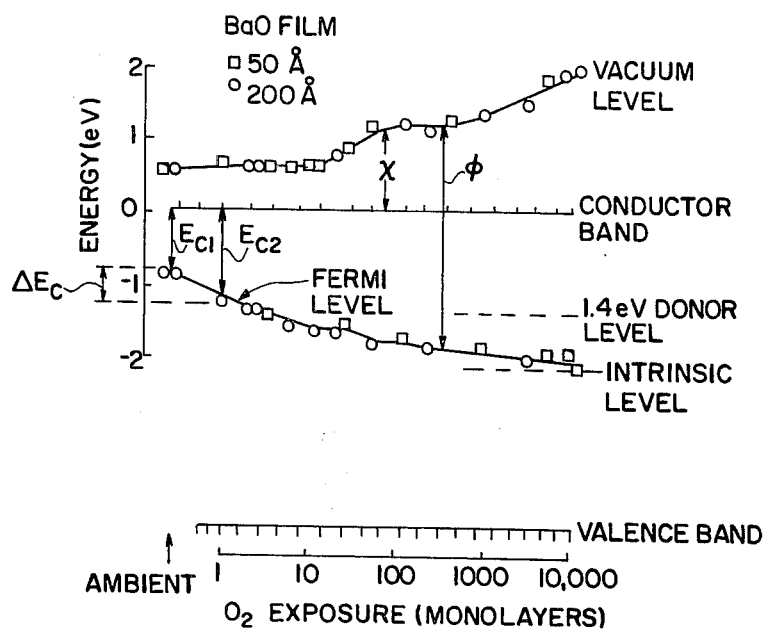
FIG. 1 is an energy-level diagram illustrating the variations in surface electronic properties of a barium-oxide film during exposure to oxygen.

The work function $\phi$ of a surface is composed of two components: (a) the position of the conduction-band edge $E_c$ with respect to the Fermi level and (b) the electron affinity $\chi$. The position of the conduction-band edge $E_c$ is governed by such band structure properties of the solid as the donor position, donor density, and ionization probability, while the electron affinity is strongly dependent on characteristics such as surface stoichiometry, surface dipole layers, and Schottky barriers. FIG. 1 is an experimentally obtained energy-level diagram showing the variation in work function $\phi$, conduction-band edge $E_c$, an electron affinity $\chi$ for a thin film (50Å to 200Å) of barium oxide (BaO) during exposure to oxygen ($O_2$). In the FIG. 1, the change in work function with $O_2$ exposure is plotted with the bottom of the conduction-band set at zero. The result is visualized as an energy-level diagram in which the Fermi level and vacuum level vary as a function of oxygen dosage. The most revealing fact is that as the $O_2$ exposure increases, the corresponding work functions also increase (the BaO is poisoned by the $O_2$). The electron affinity ($\chi = \phi - E_c$), on the other hand, remains fairly constant at the initial stages of $O_2$ exposure (through about 50 monolayers of $O_2$ exposure in this experiment), and does not change appreciably until the Fermi level approaches the asymptotic value. In the region where the electron affinity remains fairly constant, it is apparent that the changes in the work function $\phi$ are mainly due to changes in the position of the conduction-band edge $E_c$. This indicates that for small exposures to oxygen, the oxygen atoms go inside the bulk to neutralize oxygen vacancy donors. Only at higher exposures (as all the oxygen vacancies start to become filled), do the oxygen atoms start to accumulate on the surface, forming dipoles which change the electron affinity by changing the surface Ba/O stoichiometry.

The present invention is based on the foregoing characteristics of BaO. Since (1) the conductivity of the BaO is also determined by the position of the conduction-band edge with respect to the Fermi level and (2) BaO is the alkaline-earth-oxide semiconductor compound most widely used to provide low-work-function surfaces for electron emitters, the conductivity of BaO films would be an ideal indicator of the gases which fill donor sites in electron emitters. Changes in electron-emission capabilities of an emitter can therefore be predicted from changes in the conductivity of an auxiliary BaO sensor.

Figure 2:
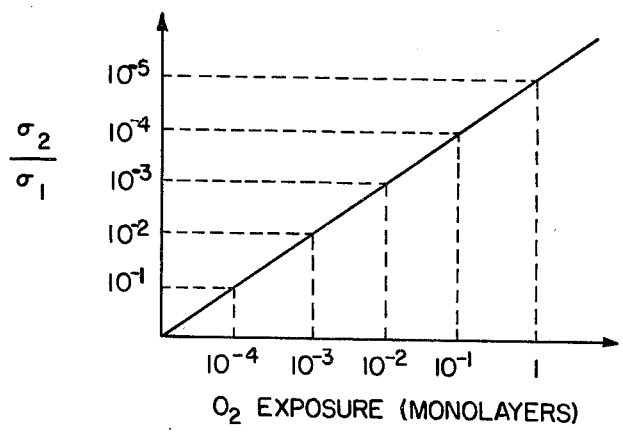
FIG. 2 is a graph illustrating the effect of oxygen exposure on the conductivity of a BaO film.

An estimate of the sensitivity to gas poisoning of BaO as represented by the conductivity of thin films may be made by considering again the experimentally obtained curves of FIG. 1. Referring specifically to the region where the electron affinity remains fairly constant although the work function changes as a function of $O_2$ exposure, the position of the conduction-band edge with respect to the Fermi level changes, with exposure to one monolayer of oxygen, from $E_{c1}$ for the activated surface to $E_{c2}$. It can be shown that the conductivities of the two surfaces are related according to $$\sigma_2/\sigma_1 \approx e^{-(E_{c2}-E_{c1})/kT}$$

where $\sigma_1$ and $\sigma_2$ are the conductivities of the activated surface and the poisoned surface, respectively, k is the Boltzmann constant, and T is the temperature. If the change ($\Delta E_c = E_{c2} - E_{c1}$) in the position of the conduction-band edge is approximately 0.5eV (estimated from FIG. 1), the ratio $\sigma_2/\sigma_1$ is $10^{-5}$ at a temperature of 500° K. Therefore, the addition of one monolayer of oxygen over the surface of these particular BaO films will cause the conductivity to change by five orders of magnitude. FIG. 2 is a plot of $\sigma_2/\sigma_1$ versus $O_2$ exposure in monolayers obtained by extrapolating this relationship to lower levels of $O_2$ exposure (assuming a linear relationship). It can be seen, for example, that for even 0.01 monolayer of contamination a three-order-of-magnitude increase in the conductivity is expected.

The electro-chemical sensor should be designed for a specific application in which it is to be used. For example, if the sensor is to be used to monitor tube-gas build-up during shelf storage, the sensitivity may be chosen to detect the contaminants in quantities that will cause actual tube failure. On the other hand, an extremely sensitive sensor may be used to monitor the vacuum quality of a tube over a short time and the results extrapolated to provide an accelerated-life-type indication of tube acceptability.

Figure 3:
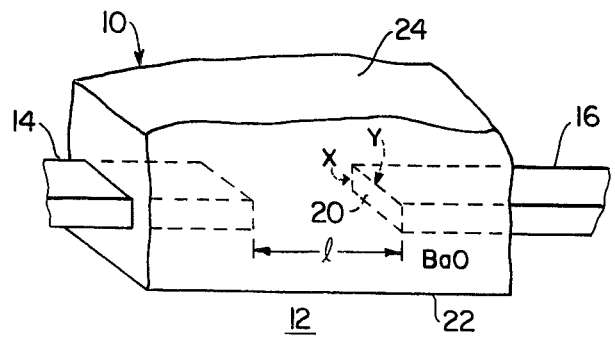
FIG. 3 is schematic view of an embodiment illustrating the basic structure of an electro-chemical sensor of the present invention.

FIG. 3 is an embodiment which may be used to illustrate factors to be considered in the design of an electro-chemical sensor according to the present invention. A barium oxide crystalline body 10 is formed on a chemically and electrically non-interacting substrate 12. A pair of electrical contacts 14 and 16, spaced apart a distance l and having opposing faces 18 and 20, respectively, are embedded in the body 10. Although the electrodes 14 and 16 are shown as separated from the BaO-substrate interface 22 in FIG. 3, this is not required and the electrodes may be adjacent to the interface 22. The volume of the body 10 between the faces 18 and 20 is defined herein as the inter-electrode volume and, in this example, is equal to the area of the opposing faces times the spacing of X·Y·l, X and Y being the dimensions of the rectangular faces.

In general the following factors should be considered in the design of the electro-chemical sensor. For a given inter-electrode volume, making the BaO surface larger will increase the sensitivity but will also increase the unwanted surface conductivity (at the free surface 24 or the interfacial surface 22). Alternatively, decreasing the interelectrode separation l for a given BaO surface area decreases the sensitivity but also reduces the unwanted surface conductivity. Increasing the temperature of the sensor by means of a heater can reduce the unwanted effects of surface conductivity but it can also reduce the sensitivity by reducing the gas sticking coefficient. However, gas mobility increases. On the other hand, unwanted internal pore conductivity will become important at the higher temperatures.

Figure 4:
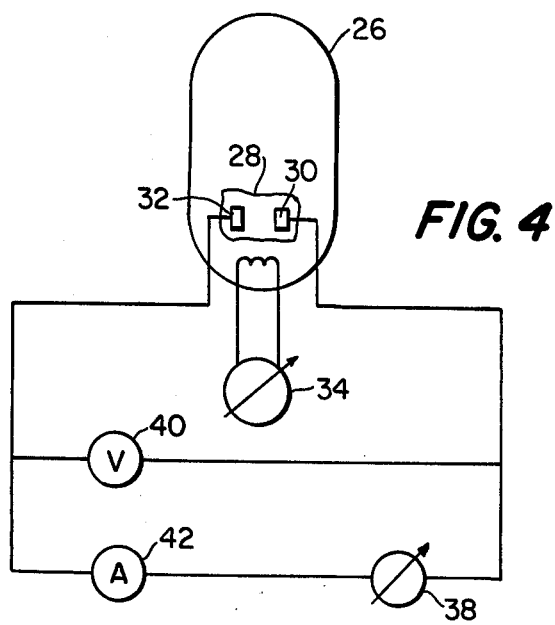
FIG. 4 is a schematic diagram illustrating the operation of the present invention.

FIG. 4 illustrates the operation of the present invention. The electro-chemical sensor, shown as a component in a vacuum tube 26, includes a BaO crystalline body 28 in which at least two electrical contacts 30 and 32 are embedded. A heater means, indicated generally by heater supply 34 and coil 36, is used to control the operating temperature of the sensor. The terminals of a source of variable potential 38 are coupled to the electrical contacts 30 and 32. A voltage meter 40 and a current meter 42 are connected in parallel and in series with the sensors, respectively, so that the conductivity may be measured. (Auxiliary voltage measuring electrodes, e.g., four-point probe type, may also be used.) The conductivity of the sensor is obtained by comparing the current passing through the interelectrode volume (i.e., the volume of the BaO between the electrical contacts 30 and 32) to the potential applied between the electrical contacts as the potential is varied. The conductivity $\sigma$ of the sensor (in the measuring volume if crystal conductivity predominates) is then related to the slope m of the current versus applied potential curve by $\sigma = m \, l/A$ where l and A are the length and cross-sectional area of the interelectrode volume, respectively. The ratio of the measured conductivity after poisoning to the original conductivity, is then a measure of the contaminating gases in the tube and also the change in work function of the emitter due to the contamination. The manner (reversibility and variation with temperature) in which the conductivity changes is different for different gases. Therefore, these characteristics can be used to identify specific gas contaminants. Such variations have, for example, been observed for oxygen, carbon dioxide and sulfur.

Figure 5:
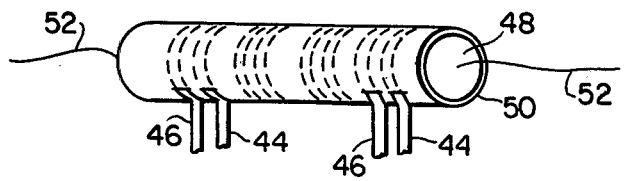
FIGS. 5, 6 and 7 are pictorial representations illustrating possible embodiments of the present invention.
Figure 6:
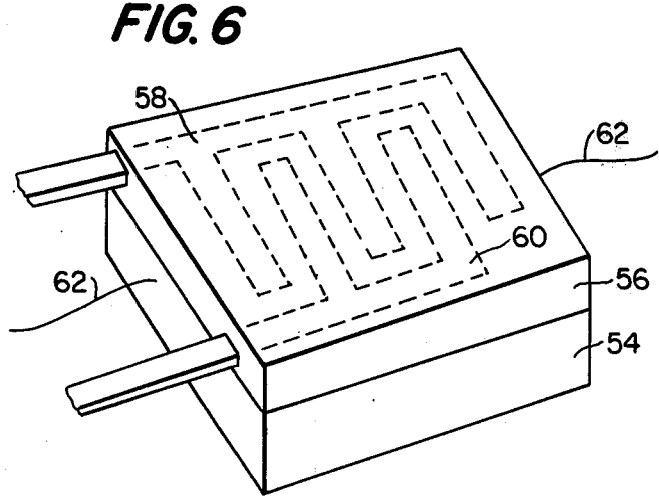
Figure 7:
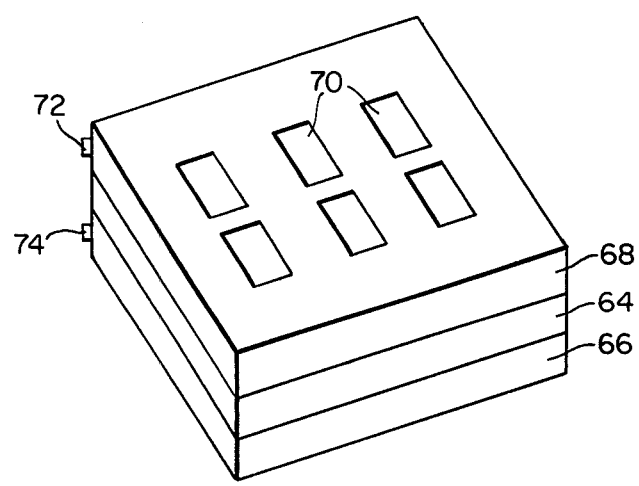

FIGS. 5, 6, and 7 each show an exemplary embodiment of an electro-chemical sensor according to the present invention. In the embodiment of FIG. 5 a pair of probe wires 44 and 46 are helically wrapped around a cylindrical non-interacting substrate 48. A film 50 of BaO is formed over the circumference of the cylinder such that the probe wires 44 and 46 are embedded in the film 50. A heating wire 52 is disposed through the non-interacting substrate 48 to permit the control of the temperature of the BaO film. In the embodiment of FIG. 6, a non-interacting substrate 54 supports a BaO film 56 which has metallic interdigital probes 58 and 60 embedded in it. It is noted that the metallic probes may or may not contact the substrate (as is also the case of the probe wires in FIG. 5). A heating wire 62 is disposed in the insulating substrate 54 to permit the control of the temperature of the BaO film. Referring to FIG. 7, a layer 64 of BaO is sandwiched between probe plates 66 and 68. The probe plates 66 and 68 have mesh openings 70 (not visible on the bottom plate 68 in the FIG. 7) which allow the gas to contact the BaO surface. Electrical contacts 72 and 74 are coupled to the probe plates 66 and 68 for measuring the conductivity of the layer 64 between the probe plates. The sensor also typically includes a means such as a heated wire (not shown) for controlling the temperature of the BaO film 64.

Obviously, many modifications and variations of the present invention are possible in light of the above teachings. It is therefore to be understood that within the scope of the appended claims, the invention may be practiced otherwise than as described.

What is claimed and desired to be secured by Letters Patent of the United States is:

1. A method of predicting a change in the work function of an emitter in a vacuum container due to contamination by gases present in said vacuum container comprising the steps of:
    exposing a body of barium oxide to the atmosphere in the vacuum container, said body having a known initial conductivity; and
    measuring the conductivity of said body after said exposure to the atmosphere in the container, a change in the conductivity indicating a change in the work function of the emitter,
    said change in work function being given approximately by the change in the conduction-band edge, $\Delta E_c$, with respect to the Fermi level of said body,
    said change in the conduction-band edge, $\Delta E_c$, being related to the ratio of the measured conductivity, $\sigma_2$, to the initial conductivity, $\sigma_1$, according to the approximation $$\sigma_2/\sigma_1 \approx e^{-(\Delta E_c)kT}$$

where k is the Boltzmann constant and T is the temperature in degrees Kelvin at which the conductivity is measured.

2. The method of claim 1 wherein the step of exposing a body of barium oxide to the atmosphere in the vacuum container comprises the step of:
    exposing a film of barium oxide formed on a noninteracting substrate to the atmosphere in the vacuum container.

3. The method of claim 1 wherein said step of measuring the conductivity of said body after exposure to the atmosphere in the vacuum container comprises the step of:
    measuring the conductivity across a predetermined volume of said body.

4. The method as recited in claim 1 wherein said emitter comprises activated barium oxide and wherein the step of exposing a body of barium oxide comprises the step of exposing a body of activated barium oxide.

5. A detector for predicting changes in the work function of an emitter in a vacuum tube due to contamination by tube gases comprising:
    a body of barium oxide having a surface which can be exposed to the atmosphere in said vacuum tube, said body having a known initial conductivity; and
    means for detecting a change in the conductivity of said body when said body is exposed to said gases, said change in conductivity being related to the change in the work function of the emitter due to contamination by said gases.

6. The detector as recited in claim 5 wherein said detecting means comprises:
    at least two spaced electrodes coupled to said body for receiving electric potential therebetween, the current between said electrodes being dependent on the conductivity of said barium oxide body.

7. The detector as recited in claim 5 wherein said barium oxide body is electrically active.

8. The detector as recited in claim 7 wherein said barium oxide body is a thin film of barium oxide formed on a noninteracting substrate.

9. A method of detecting gases which contaminate an emitter in a vacuum container comprising the steps of:
    exposing a body of barium oxide to the atmosphere in the container, said body having a known initial conductivity; and
    measuring the conductivity of said body after exposure to the atmosphere, a change in the conductivity due to exposure to the atmosphere indicating the presence of contaminating gas and the amount of the change being related to the quantity of gas molecules contaminating contaminating said emitter.

10. A method of detecting the quantity of oxygen molecules contaminating an emitter in a vacuum container comprising the steps of:
    exposing a thin film of barium oxide to the atmosphere in the container, said film of barium oxide having a known initial conductivity, and
    measuring the conductivity of said film of barium oxide after exposure to the atmosphere, a change in the conductivity due to exposure to the atmosphere indicating the presence of oxygen and the amount of the change being related to the quantity of oxygen molecules contaminating said emitter,
    a ten-fold decrease in the ratio of the measured conductivity $\sigma_2$ to the initial conductivity $\sigma_1$ indicating a ten-fold increase in the quantity of oxygen molecules contaminating said emitter.

* * * * *